US007799756B2

(12) United States Patent
Molino et al.

(10) Patent No.: US 7,799,756 B2
(45) Date of Patent: Sep. 21, 2010

(54) PROCESSES FOR STEREOSELECTIVE SYNTHESIS OF TRANS ISA$_{TX}$247

(75) Inventors: Bruce F. Molino, Slingerlands, NY (US); Zhicai Yang, Schenectady, NY (US); Jun-Ho Maeng, Cohoes, NY (US); David D. Manning, Duanesburg, NY (US)

(73) Assignee: Albany Molecular Research, Inc., Albany, NY (US)

( * ) Notice: Subject to any disclaimer, the term of this patent is extended or adjusted under 35 U.S.C. 154(b) by 803 days.

(21) Appl. No.: 11/572,833

(22) PCT Filed: Jul. 26, 2005

(86) PCT No.: PCT/US2005/026319

§ 371 (c)(1),
(2), (4) Date: May 10, 2007

(87) PCT Pub. No.: WO2006/014872

PCT Pub. Date: Feb. 9, 2006

(65) Prior Publication Data

US 2008/0021197 A1    Jan. 24, 2008

Related U.S. Application Data

(60) Provisional application No. 60/592,330, filed on Jul. 29, 2004.

(51) Int. Cl.
A61K 38/13      (2006.01)
A61K 38/12      (2006.01)
(52) U.S. Cl. .............................. 514/9; 514/11; 530/317
(58) Field of Classification Search ....................... None
See application file for complete search history.

(56) References Cited

U.S. PATENT DOCUMENTS 6,613,739 B1 *  9/2003  Naicker et al. ................. 514/11
2004/0220091 A1 * 11/2004  Adam et al. ................... 514/11

FOREIGN PATENT DOCUMENTS

WO          03/033526 A2      4/2003

OTHER PUBLICATIONS

Aspeslet, Transplantation Proceedings, 33, 1048-1051 (2001).*

* cited by examiner

Primary Examiner—Andrew D Kosar
Assistant Examiner—Satyanarayana R Gudibande
(74) Attorney, Agent, or Firm—Nixon Peabody LLP

(57) ABSTRACT

The present invention relates to a process for preparation of a trans ISA$_{TX}$247 compound of the formula: where $R_1$=H or D; $R_2$=H or D; and $R_3$=H or D, by application of organozirconium chemistry. The process involves reacting an acetyl cyclosporin aldehyde with an organozirconium reagent to provide acetyl cyclosporin diene (the acetate of trans ISA$_{TX}$247) and deacetylating the acetyl cyclosporin diene to produce the trans-isomer of ISA$_{TX}$247. The present invention also relates to a process for preparing the same trans ISA$_{TX}$247 compound, using olefin cross metathesis. The process involves: olefin cross metathesis of acetyl cyclosporin A to afford acetyl cyclosporin α,β-unsaturated aldehyde; Wittig reaction of the acetyl cyclosporin α,β-unsaturated aldehyde to provide acetyl cyclosporin diene; and deacetylation of the acetyl cyclosporin diene to produce the trans ISA$_{TX}$247 compound. Also disclosed are processes for preparing an acetyl cyclosporin α,β-unsaturated aldehyde compound and a cyclosporin triene analogue compound.

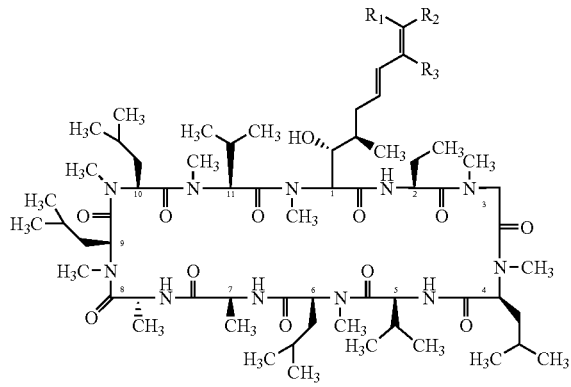

(I)

24 Claims, No Drawings

PROCESSES FOR STEREOSELECTIVE SYNTHESIS OF TRANS ISA$_{TX}$247

This application claims the priority benefit of U.S. Provisional Patent Application Ser. No. 60/592,330, filed Jul. 29, 2004, which is hereby incorporated by reference in its entirety.

FIELD OF THE INVENTION

The present invention provides novel processes for stereoselective preparation of trans ISA$_{TX}$247 (the trans-isomer of ISA$_{TX}$247), which is a known drug candidate for immunosuppression and treatment of other diseases.

BACKGROUND OF THE INVENTION

Novel cyclosporin analogue, ISA$_{TX}$247, is a mixture of cis and trans isomers of cyclosporin diene analogue, which is chemically described as cyclo {(E,Z)-(2S,3R,4R)-3-hydoxy-4-methyl-2-(methylamino)-6,8-nonadienoyl-L-2-aminobutyryl-N-methyl-glycyl-N -methyl-L-leucyl-L-valyl-N-methyl-L-leucyl-L-alanyl-D-alanyl-N-methyl-L-leucyl-N-methyl-L-leucyl-N-methyl-L-valyl}. It is remarkable that the mixture of ISA$_{TX}$247 isomers exhibits a combination of enhanced potency and reduced toxicity over natural cyclosporins and presently known cyclosporin derivatives (Abel et al., "ISA$_{TX}$247: A Novel Calcineurin Inhibitor," *J. Heart Lung Transplant,* 20:161 (2001); Aspeslet et al., "ISA$_{TX}$247: A Novel Calcineurin Inhibitor," *Transplantation Proceedings,* 33:1048-1051 (2001); U.S. Pat. Nos. 6,605,593 and 6,613,739 to Naicker et al.).

ISA$_{TX}$247, as a mixture of cis and trans isomers, is currently being co-developed by Roche and Isotechnika for treatment of multiple diseases. The drug candidate has successfully completed a phase II clinical trial for psoriasis and achieved positive results in one phase II (phase IIa) clinical trial for kidney transplantation. The main phase IIb clinical trial in kidney transplantation is due to begin soon.

In the course of the collaboration between Roche and Isotechnika for the clinical development and commercialization of ISA$_{TX}$247, a formulation of the trans ISA$_{TX}$247 (the trans-isomer of ISA$_{TX}$247) has been developed. Based on a restructured collaboration between the two companies, clinical trials for both kidney transplantation and treatment of psoriasis by such formulations of trans ISA$_{TX}$247 are under way. Compared to the corresponding cis-isomer, the trans-isomer of ISA$_{TX}$247 (trans ISA$_{TX}$247) has shown better activity on immunosuppression and improved therapeutic index. The interesting biological properties and the potential pharmaceutical utility of trans ISA$_{TX}$247 make it important to develop new methods for stereoselective synthesis of this drug candidate.

There are several synthetic pathways known in literature for the preparation of ISA$_{TX}$247 as a mixture of cis and trans isomers, some of which involving a Wittig reaction of either acetyl cyclosporin aldehyde or triphenylphosphonium bromide of acetyl cyclosporin A (U.S. Pat. Nos. 6,605,593 and 6,613,739 to Naicker et al.; PCT International Publication Nos. WO 03/033526 and WO 03/033527 to Naicker et al.). However, only very few methods for stereoselective synthesis of the trans-isomer of ISA$_{TX}$247, such as the application of Peterson olefination, have been developed (PCT International Publication Nos. WO 03/033526 and WO 03/033527 to Naicker et al.).

The present invention is directed to overcoming these deficiencies in the art.

SUMMARY OF THE INVENTION

The present invention relates to a process for preparation of a trans ISA$_{TX}$247 compound of the formula:

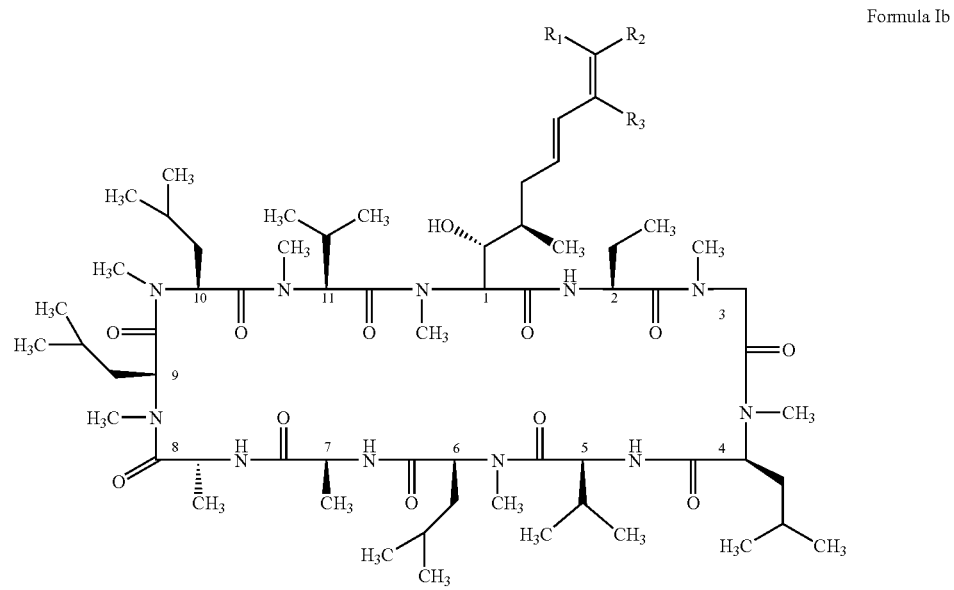

Formula Ib where $R_1$=H or D; $R_2$=H or D; and $R_3$=H or D. The process involves reacting a first intermediate compound of the formula:

Another aspect of the present invention relates to a process for preparation of a trans $ISA_{TX}247$ compound of the formula:

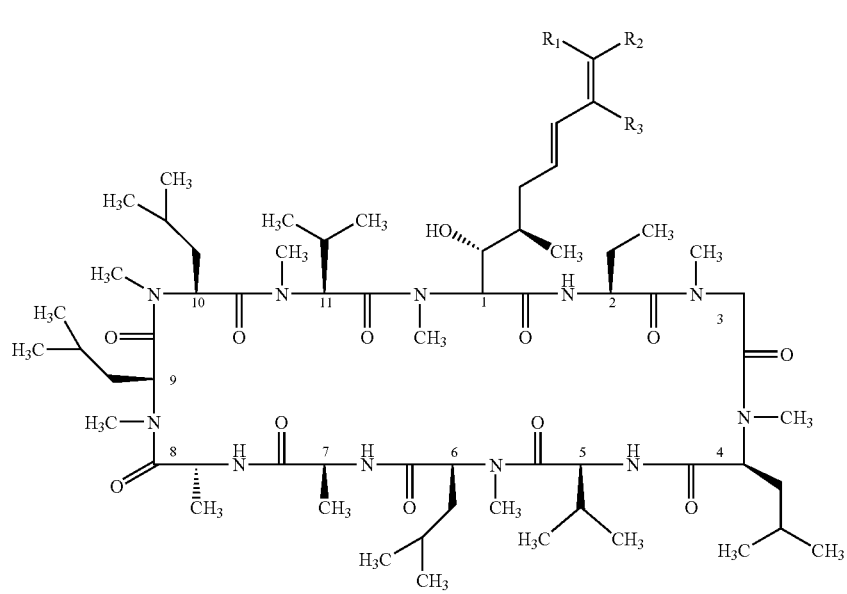

Formula Ib where $R_1$=H or D; $R_2$=H or D; and $R_3$=H or D. The process involves carrying out olefin cross metathesis of a first intermediate compound of the formula:

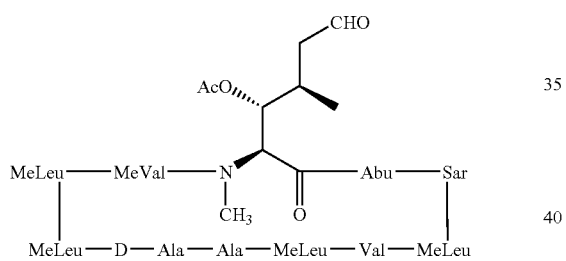

with an organozirconium reagent, under conditions effective to produce a second intermediate compound of the formula:

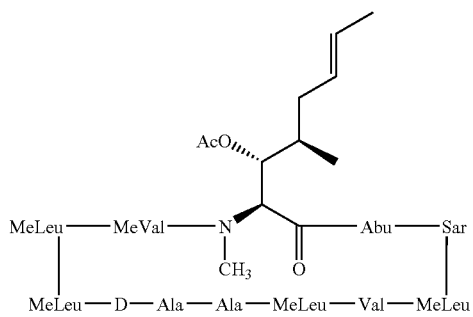

under conditions effective to produce a second intermediate compound of the formula:

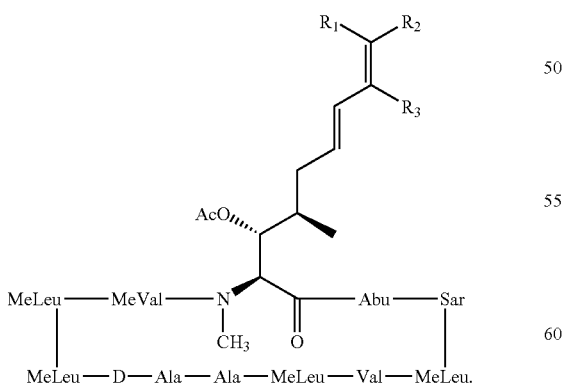

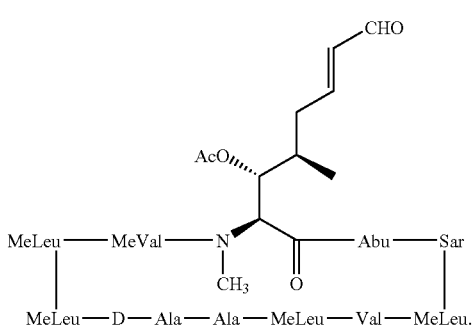

Then, the second intermediate compound is deacetylated, under conditions effective to produce the trans $ISA_{TX}247$ compound.

Next, a Wittig reaction is carried out on the second intermediate compound, under conditions effective to produce a third intermediate compound of the formula:

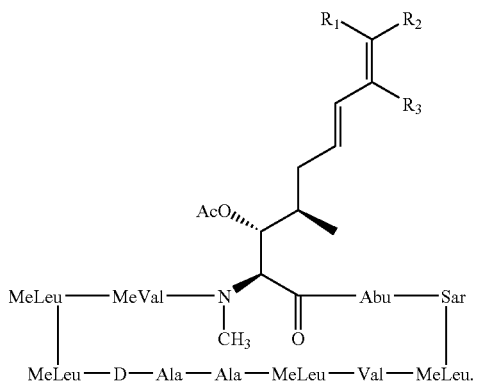

Then, the third intermediate compound is deacetylated, under conditions effective to produce the trans $ISA_{TX}247$ compound.

Another aspect of the present invention relates to a process for preparation of an acetyl cyclosporin α,β-unsaturated aldehyde compound of the formula:

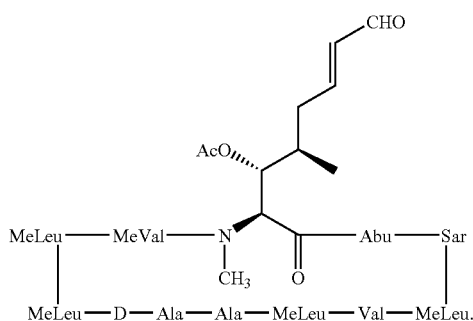

The process involves reacting a first intermediate compound of the formula:

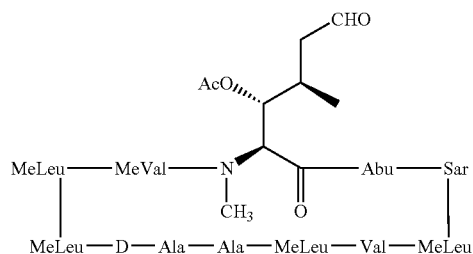

with an organozirconium reagent, under conditions effective to produce the acetyl cyclosporin α,β-unsaturated aldehyde compound.

The present invention also relates to a process for preparing a cyclosporin triene analogue compound of the formula:

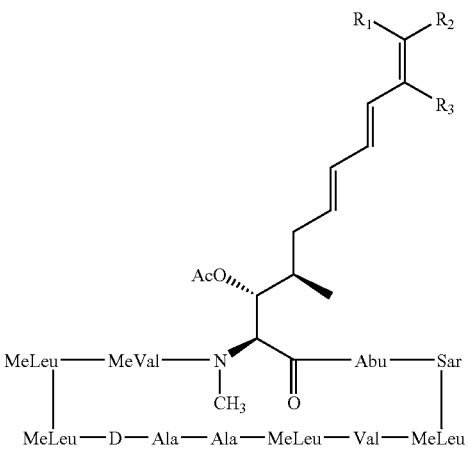

where $R_1$=H or D; $R_2$=H or D; and $R_3$=H or D. The process involves reacting a first intermediate compound of the formula:

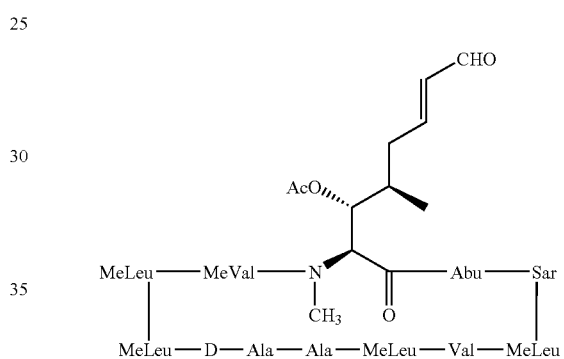

with an organozirconium reagent, under conditions effective to produce the cyclosporin triene analogue compound.

The present invention discloses novel methods for stereoselective preparation of trans $ISA_{TX}247$ (the trans isomer of $ISA_{TX}247$), a drug candidate as an immunosuppressive agent and for treatment of other diseases such as psoriasis. In particular, the present invention relates to novel processes for preparing such a drug candidate by application of organozirconium chemistry or olefin cross metathesis as the key step.

The methods of the present invention have good overall yield and high stereoselectivity. The reactions in the synthetic pathways of the present invention are facile and conducted under mild reaction conditions. The drug candidate prepared via these synthetic routes is the pure trans-isomer of $ISA_{TX}247$.

DETAILED DESCRIPTION OF THE INVENTION $ISA_{TX}247$, as a mixture of cis and trans isomers, can be represented by Formula (I), as shown below. The wavy bond in the structure indicates that the diene system can be either cis-configuration (Z-configuration) or trans-configuration (E-configuration). In the present application, the terms cis-isomer (or cis-configuration) and Z-isomer (or Z-configuration) will be used interchangeably and the terms trans-isomer (or trans-configuration) and E-isomer (or E-configuration) are also interchangeable.

Formula I

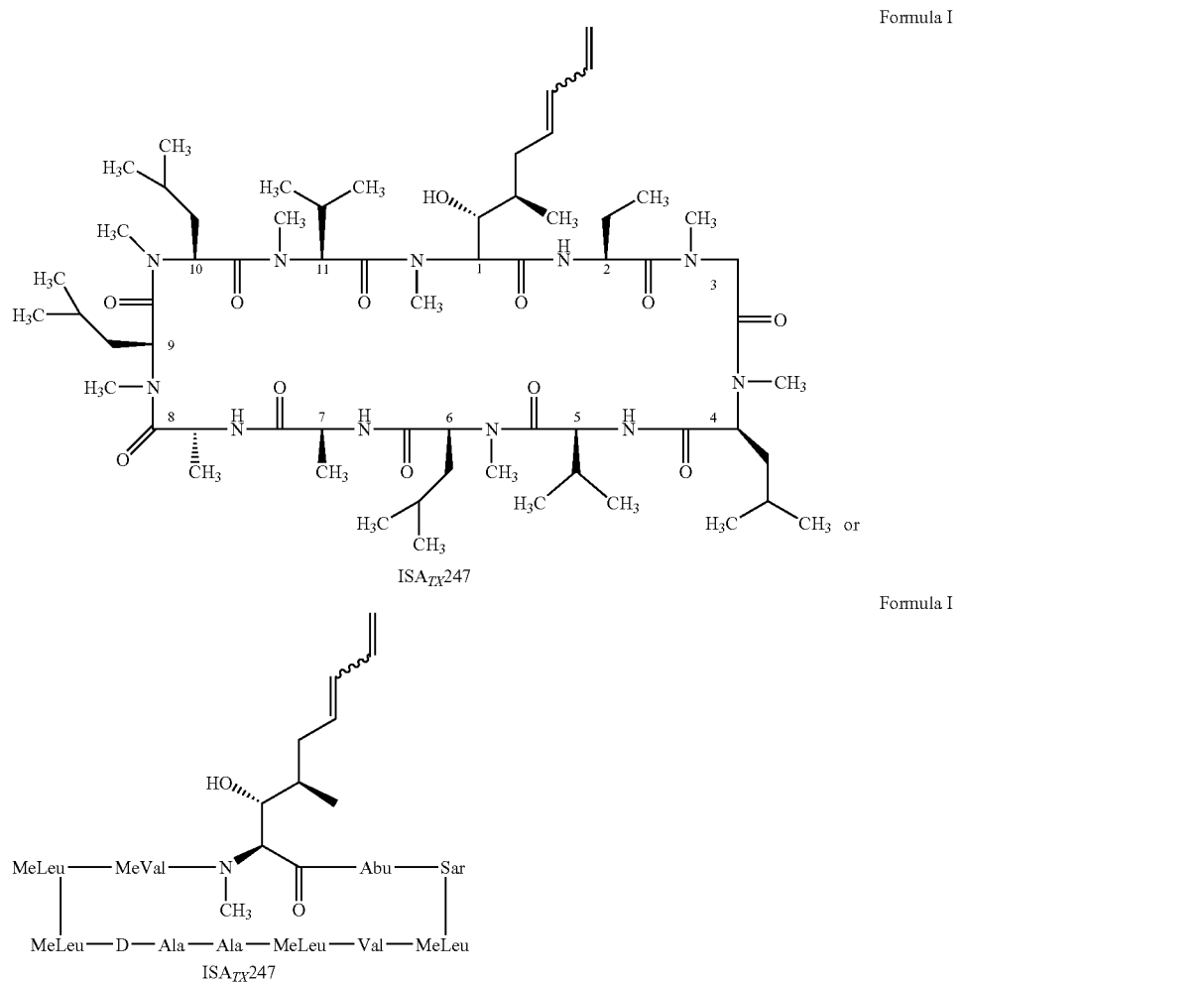

The structures of the cis-isomer of ISA$_{TX}$247 (cis ISA$_{TX}$247) and the trans-isomer of ISA$_{TX}$247 (trans ISA$_{TX}$247) are shown below as Formula (Ia) and Formula (Ib), respectively.

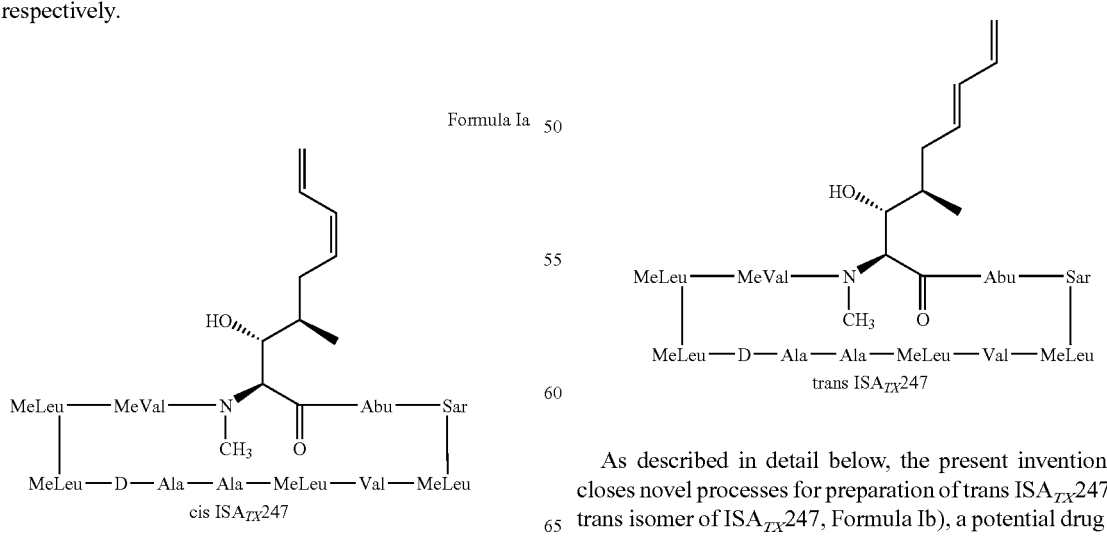

As described in detail below, the present invention discloses novel processes for preparation of trans ISA$_{TX}$247 (the trans isomer of ISA$_{TX}$247, Formula Ib), a potential drug with utility for treatment of various diseases. The synthetic routes of the present invention possess many advantages, such as good yield, high stereoselectivity, mild conditions, low cost, and capability for large scale synthesis.

The starting material used in the disclosed synthetic methods of the present invention is cyclosporin A, which is represented by Formula (II). According to one embodiment of the present invention, trans $ISA_{TX}247$ can be prepared by the application of organozirconium chemistry as the key step in a four-step synthetic pathway, as shown below in Scheme 1.

The first step of the above reaction scheme is the protection of the free hydroxyl group of cyclosporin A. Acetyl group is one of the most commonly used protection groups for alcohol, although other methods could be also applied here to protect cyclosporin A. Treatment of cyclosporin A with excess acetic anhydride in methylene chloride at room temperature using pyridine as a base and 4-dimethylaminopyridine as a catalyst provides acetyl cyclosporin A in excellent

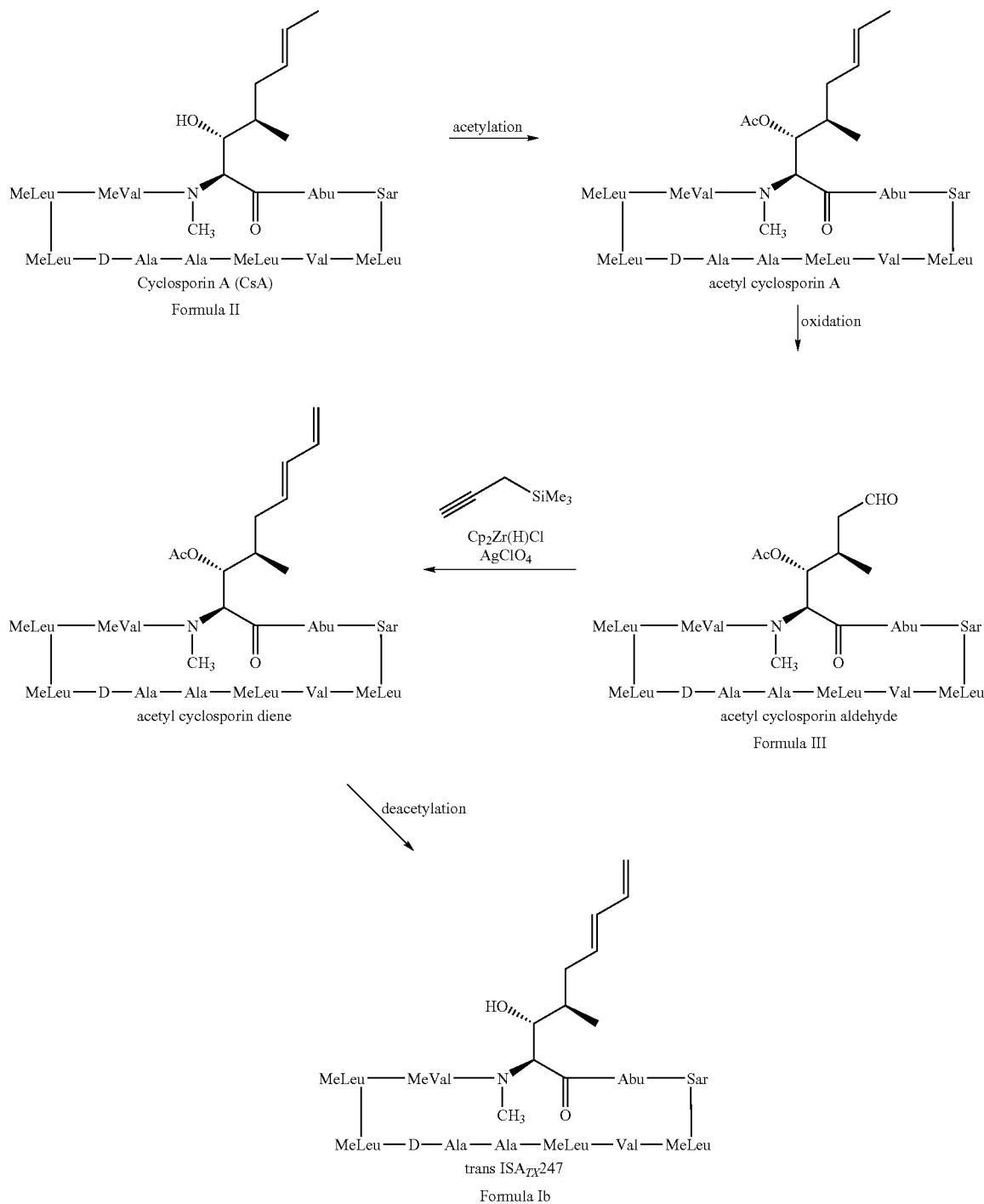

yield. After a standard work-up, the crude product can be used in the next step without purification.

In order to convert acetyl cyclosporin A to acetyl cyclosporin aldehyde in the next step, an oxidation is carried out to cleave the carbon-carbon double bond in the side chain of the first amino acid of cyclosporin A. Among the methods to do so, ozonolysis is a popular reaction to use. Treatment of acetyl cyclosporin A with ozone in methylene chloride at −78° C., followed by reductive work-up with methyl sulfide generates the desired acetyl cyclosporin aldehyde in excellent yield. The product is pure enough to be carried over to the next step without purification.

The key step of the above reaction scheme is the application of organozirconium chemistry (Maeta et al., *Tetrahedron Letters*, 33:5969-5972 (1992), which is hereby incorporated by reference in its entirety) to acetyl cyclosporin aldehyde, which is proven to be an excellent method to transform acetyl cyclosporin aldehyde into acetyl cyclosporin diene (the acetate of ISA$_{TX}$247) in good yield and high stereoselectivity. Under these mild reaction conditions (the reaction is conducted at room temperature), a single trans-isomer of acetyl cyclosporin diene (the acetate of trans ISA$_{TX}$247) is provided with no cis-isomer observed by proton nuclear magnetic resonance (NMR) studies. The reagents used in this reaction (such as propargyl trimethylsilane and Cp$_2$Zr(H)Cl) are common and commercially available. The catalyst of the reaction is a silver salt. The silver salt can be selected from silver perchlorate (AgClO$_4$), AgOTf, AgBF$_4$, AgPF$_6$, AgAsF$_6$, AgSbF$_6$, or any other silver salts.

As the final step of this synthetic pathway, the acetyl protection group is removed. Treatment of acetyl cyclosporin diene (the acetate of trans ISA$_{TX}$247) with potassium carbonate in methanol at room temperature affords the desired trans ISA$_{TX}$247 (Formula Ib) in good yield and in exclusively trans-configuration (E-configuration).

Utilizing the same strategy, deuterated analogues of trans ISA$_{TX}$247 can be prepared by employing deuterated reagents. As shown in Scheme 2, reaction of acetyl cyclosporin aldehyde of Formula III with deuterated zirconium reagent (Cp$_2$Zr(D)Cl) or deuterated propargyl trimethylsilane in the presence of silver perchlorate generates acetate of mono or di-deuterated trans ISA$_{TX}$247, respectively. Treatment of acetyl cyclosporin aldehyde with both deuterated zirconium reagent and deuterated propargyl trimethylsilane provides acetate of tri-deuterated trans ISA$_{TX}$247.

As shown in Scheme 3, such a deuterated propargyl trimethylsilane can be readily prepared from the commercially available trimethylsilyl acetylene, following a procedure for preparing similar compounds (Rajagopalan et al., *Synthesis,* 2:111-112 (1984), which is hereby incorporated by reference in its entirety).

Scheme 3

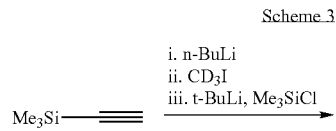

-continued

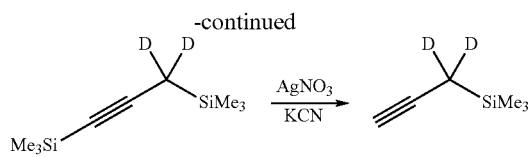

According to another embodiment of the present invention, the trans $ISA_{TX}247$ can be prepared via an alternative approach employing olefin cross metathesis (Scheme 4), which is also a four-step synthetic pathway starting from protection of the alcohol of cyclosporin A, as described above in Scheme 1. The key step of this synthetic approach is olefin cross metathesis of acetyl cyclosporin A to provide acetyl cyclosporin α,β-unsaturated aldehyde in trans configuration (E-configuration).

Scheme 4

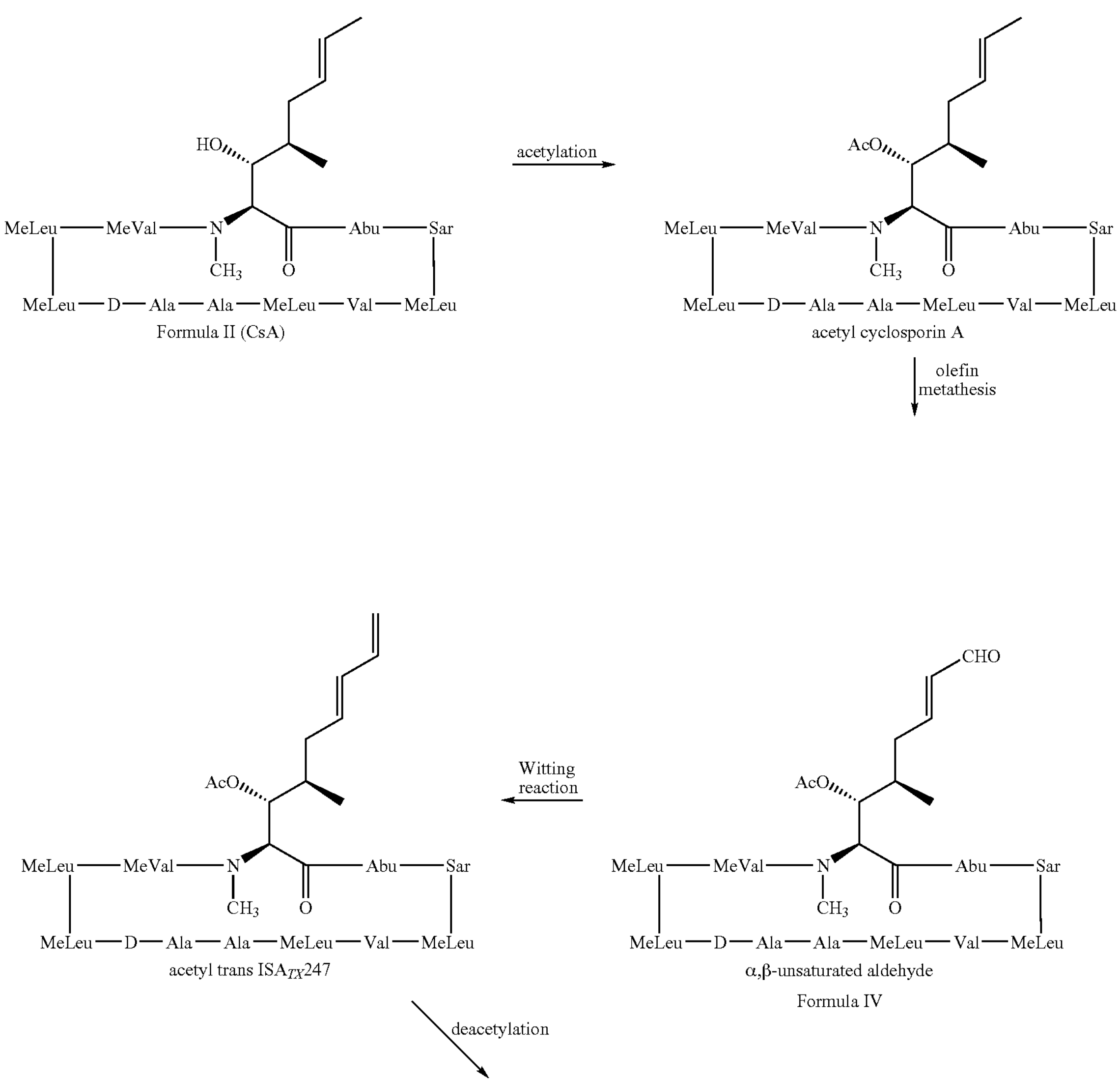

Formula II (CsA)

acetyl cyclosporin A

α,β-unsaturated aldehyde

Formula IV acetyl trans $ISA_{TX}247$

-continued

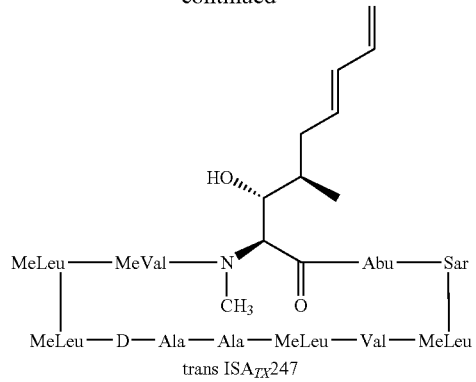

trans $ISA_{TX}247$

In the last decade, ruthenium-catalyzed olefin metathesis has emerged as a powerful synthetic tool for the formation of carbon-carbon bonds (Chatterjee et al., "A General Model for Selectivity in Olefin Cross Metathesis," *J. Am. Chem. Soc.*, 125:11360-11370 (2003); Connon et al., "Recent Development in Olefin Cross Metathesis," *Angew. Chem. Int. Ed.*, 42:1900-1923 (2003), which are hereby incorporated by reference in their entirety). There are three main variations on olefin metathesis: (a) cross metathesis; (b) ring opening/close metathesis; and (c) intermolecular enyne metathesis. As an acyclic carbon-carbon bond-forming method, olefin cross metathesis has numerous advantages: (1) the process is catalytic (typically 1-5 mol % of catalyst required); (2) high yield can be obtained under mild conditions in a relatively short reaction time; (3) a wide range of functional groups are tolerated, with minimal substrate protection necessary; and (4) the reaction is relatively atom-economic and gaseous ethylene is usually the only byproduct, which is an important consideration in industrial applications (Connon et al., "Recent Development in Olefin Cross Metathesis," *Angew. Chem. Int. Ed.*, 42:1900-1923 (2003), which is hereby incorporated by reference in its entirety).

Olefin cross metathesis of acetyl cyclosporin A is carried out with acrolein acetal (such as acrolein dimethyl acetal, acrolein diethyl acetal, and 2-vinyl-1,3-dioxolane) in the presence of Grubbs' catalyst in solvents such as methylene chloride, chloroform, toluene, and tetrahydrofuran (THF). The reaction provides an acetal intermediate which is hydrolyzed during purification by high pressure liquid chromatography using acetonitrile-water-trifluoroacetic acid as the solvent system to afford trans-α,β-unsaturated aldehyde of Formula IV directly in good to excellent yield (60-80%). The cyclosporin acetal intermediate from this reaction can be also transformed into the desired trans cyclosporin α,β-unsaturated aldehyde by treatment with a strong acid (such as hydrochloric acid, sulfuric acid, or trifluoroacetic acid). The catalyst can be either Grubbs' catalyst (Schwab et al., "A Series of Well-Defined Metathesis Catalysts-Synthesis of $[RuCl_2(=CHR')(PR_3)_2]$ and Its Reactions," *Angew. Chem. Int. Ed.*, 34:2039-2041 (1995), which is hereby incorporated by reference in its entirety), Hoveyda-Grubbs' catalyst (Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Org. Lett.*, 1:953 (1999); Sanford et al., "Mechanism and Activity of Ruthenium Olefin Metathesis Catalysts," *J. Am. Chem. Soc.*, 123:6543-6554 (2001), which are hereby incorporated by reference in their entirety), or other ruthenium, molybdenum, and tungsten catalysts. This stereoselective chemistry provides an α,β-unsaturated aldehyde of Formula IV in exclusively the trans-configuration. There is no corresponding cis isomer observed by proton nuclear magnetic resonance (NMR) studies.

As shown in Scheme 4, Wittig reaction of cyclosporin α,β-unsaturated aldehyde of Formula IV in the next step provides acetate of $ISA_{TX}247$ as the desired trans isomer smoothly. The phosphorus ylide for Wittig reaction can be generated by treatment of the corresponding methyltriphenylphosphonium salt (such as $CH_3PPh_3Cl$, $CH_3PPh_3Br$ and $CH_3PPh_3I$) with a strong base, such as butyllithium and sodium bis(trimethylsilyl)amide. Using this strategy, the deuterated trans $ISA_{TX}247$ ($ISA_{TX}247\text{-}d_2$) can be prepared by application of the corresponding deuterated methyltriphenylphosphonium salt (such as $CD_3PPh_3Cl$, $CD_3PPh_3Br$ and $CD_3PPh_3I$).

Finally, the acetyl protection group can be removed with potassium carbonate in methanol to produce trans $ISA_{TX}247$, as described above for Scheme 1.

Another aspect of the present invention relates to an alternative method for preparing the cyclosporin α,β-unsaturated aldehyde of Formula IV employing organozirconium chemistry, as shown in Scheme 5. Reaction of the acetyl cyclosporin aldehyde of Formula III with a commercially available alkyne reagent, such as methoxyethyne and ethoxyethyne, and a zirconium reagent ($Cp_2Zr(H)Cl$) in the presence of a silver salt catalyst (e.g. $AgClO_4$, AgOTf, $AgBF_4$, $AgPF_6$, $AgAsF_6$, and $AgSbF_6$), followed by an acid treatment, provides cyclosporin α,β-unsaturated aldehyde of Formula IV in exclusively the trans configuration.

Scheme 5 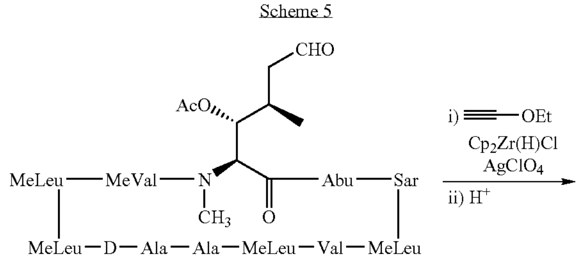 acetyl cyclosporin aldehyde

Formula III

-continued

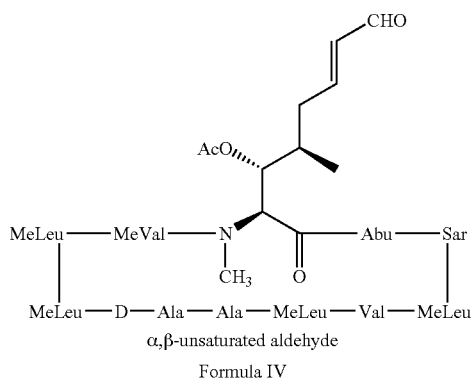

α,β-unsaturated aldehyde
Formula IV

The present invention also relates to a novel process for preparation of a cyclosporin triene analogue of Formula V (U.S. Pat. Nos. 6,605,593 and 6,613,739 to Naicker et al., which are hereby incorporated by reference in their entirety), utilizing methods provided in the present invention: Similar to the conversion of acetyl cyclosporin aldehyde of Formula III to acetyl cyclosporin diene with a zirconium reagent (Scheme 1), application of organozirconium chemistry to the acetyl cyclosporin α,β-unsaturated aldehyde of Formula IV leads to a facile preparation of cyclosporin triene of Formula V, as shown by Scheme 6.

Scheme 6

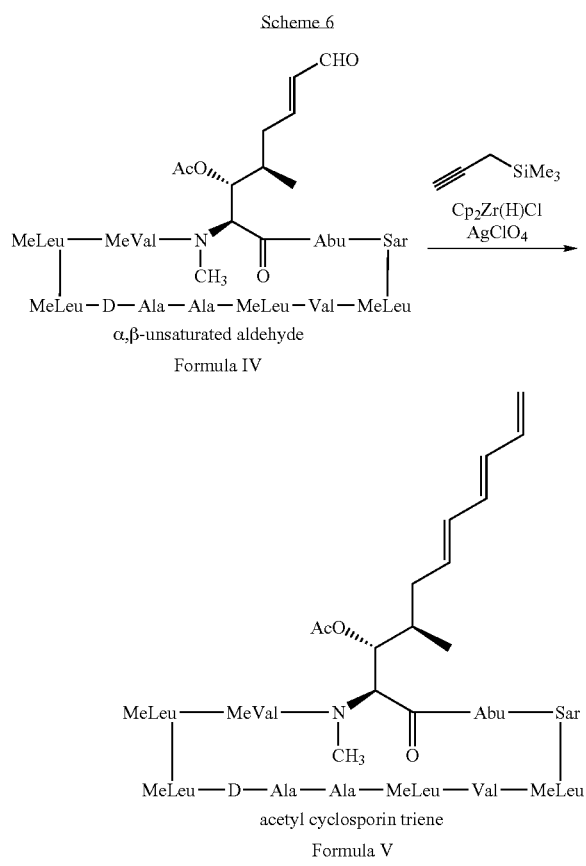

EXAMPLES

The following examples are provided to illustrate embodiments of the present invention but are by no means intended to limit its scope.

Example 1

Preparation of Acetyl Cyclosporin A

A solution of cyclosporin A (5.0 g, 4.16 mmol), acetic anhydride (3.92 mL, 41.6 mmol), pyridine (3.36 mL, 41.6 mmol), and DMAP (0.5 g, 4.2 mmol) in methylene chloride (20 mL) was stirred overnight at room temperature under $N_2$ atmosphere. Saturated sodium bicarbonate solution (200 mL) was added to the solution and stirred for an additional 2 h. The mixture was extracted with ether, washed with 1 N HCl, neutralized with saturated sodium bicarbonate solution, washed with brine, dried over sodium sulfate, and concentrated in vacuo to afford acetyl cyclosporin A (4.92 g, 95%) as a white solid, which was carried to the next step without further purification: $^1$H NMR (300 MHz, CDCl$_3$) δ 8.57 (d, J=9.6 Hz, 1H), 8.04 (d, J=6.9 Hz, 1H), 7.51 (d, J=9.4 Hz, 1H), 7.47 (d, J=7.8 Hz, 1H), 5.67 (dd, J=11.0, 4.0 Hz, 1H), 5.60-5.44 (m, 2H), 5.39 (dd, J=11.7, 3.7 Hz, 1H), 5.32-5.13 (m, 4H), 5.06-4.93 (m, 2H), 4.85 (t, J=7.2 Hz, 1H), 4.77 (t, J=9.6 Hz, 1H), 4.65 (d, J=13.7 Hz, 1H), 4.41 (t, J=7.0 Hz, 1H), 3.46 (s, 3H), 3.26 (s, 3H), 3.24 (s, 3H), 3.21 (s, 3H), 3.10 (s, 3H), 2.68 (s, 3H), 2.66 (s, 3H), 2.50-2.35 (m, 1H), 2.25-1.80 (m, 6H), 2.08 (s, 3H), 2.01 (s, 3H), 1.75-1.55 (m, 6H), 1.45-0.75 (m, 55H); ESI MS m/z 1245 [C$_{64}$H$_{113}$N$_{11}$O$_{13}$+H]$^+$.

Example 2

Preparation of Acetyl Cyclosporin Aldehyde

Ozone was bubbled into a solution of acetyl cyclosporin from Example 1 (3.0 g, 2.4 mmol) in methylene chloride (70 mL) at −78° C. until a blue color was developed. The mixture was degassed with nitrogen for a few minutes and dimethylsulfide (3 mL) was added at −78° C. The reaction mixture was allowed to warm to room temperature and stirred for 3 h. The reaction mixture was concentrated in vacuo and the residue was dissolved in ethyl acetate (300 mL), washed with water (2×70 mL) and brine (70 mL), dried over sodium sulfate, filtered, and concentrated in vacuo to afford acetyl cyclosporin aldehyde (2.79 g, 94%) as a white solid, which was carried to the next step without further purification: $^1$H NMR (300 MHz, CDCl$_3$) δ 9.60 (d, J=3.5 Hz, 1H), 8.55 (d, J=9.7 Hz, 1H), 7.96 (d, J=6.8 Hz, 1H), 7.52 (d, J=7.7 Hz, 1H), 7.46 (d, J=9.0 Hz, 1H), 5.67 (dd, J=11.0, 3.8 Hz, 1H), 5.60-5.45 (m, 2H), 5.32 (dd, J=12.1, 3.3 Hz, 1H), 5.24-5.10 (m, 2H), 5.08-4.90 (m, 2H), 4.84 (t, J=7.1 Hz, 1H), 4.73 (t, J=9.6 Hz, 1H), 4.64 (d, J=13.8 Hz, 1H), 4.41 (t, J=7.0 Hz, 1H), 3.46 (s, 3H), 3.29 (s, 6H), 3.21 (s, 3H), 3.08 (s, 3H), 2.67 (s, 3H), 2.65 (s, 3H), 2.50-2.35 (m, 2H), 2.25-1.80 (m, 6H), 1.99 (s, 3H), 1.75-1.55 (m, 3H), 1.50-0.75 (m, 57H); ESI MS m/z 1233 [C$_{62}$H$_{109}$N$_{11}$O$_{14}$+H]$^+$.

Example 3

Preparation of Acetyl Cyclosporin Diene

To a suspension of bis(cyclopentadienyl)zirconiumchloride hydride (620 mg, 2.40 mmol) in methylene chloride (5 mL) was added propargyltrimethylsilane (0.38 mL, 2.5 mmol), and then the mixture was stirred at room temperature for 10 min. To this solution was sequentially added a solution of acetyl cyclosporin aldehyde from Example 2 (300 mg, 0.240 mmol) in methylene chloride (1 mL) and then silver perchlorate (10 mg, 0.050 mmol). The resulting mixture was stirred at room temperature for 18 h, and then poured into a saturated solution of sodium bicarbonate (10 mL). The organic layer was separated and the aqueous layer was extracted with methylene chloride (3×20 mL). The combined organics were dried over anhydrous sodium sulfate and concentrated under vacuum to afford the crude product. The material was purified by semi-preparative HPLC to afford the acetate of trans ISA$_{TX}$247 (140 mg, 47%) as a pale-brown oil: $^1$H NMR (300 MHz, CDCl$_3$) δ 8.46 (d, J=9.1 Hz, 1H), 8.05 (d, J=7.1 Hz, 1H), 7.78 (d, J=9.0 Hz, 1H), 7.57 (d, J=7.8 Hz, 1H), 6.21 (dt, J=16.8, 10.3 Hz, 1H), 5.90 (dd, J=14.9, 10.8 Hz, 1H), 5.69 (dd, J=10.7, 3.6 Hz, 1H), 5.54 (s, 2H), 5.40-4.75 (m, 7H), 4.65 (d, J=14.2 Hz, 1H), 4.46 (t, J=7.3 Hz, 1H), 3.44 (s, 3H), 3.25 (s, 3H), 3.19 (s, 6H), 3.11 (s, 3H), 2.69 (s, 6H), 2.48-2.33 (m, 1H), 2.22-2.09 (m, 5H), 2.02 (s, 3H), 1.75-0.70 (m, 65H); ESI MS m/z 1257 [C$_{65}$H$_{113}$N$_{11}$O$_{13}$+H]$^+$.

Example 4

Preparation of trans ISA$_{TX}$247

To a stirred solution of the acetate of trans ISA$^{TX}$247 from Example 3 (74 mg, 0.060 mmol) in methanol (8 mL) was added potassium carbonate (204 mg, 1.48 mmol) at room temperature. After 12 h at room temperature, methanol was evaporated. The crude product was diluted in water (15 mL) and extracted with ethyl acetate (3×50 mL). The combined organics were dried over anhydrous sodium sulfate, and concentrated under vacuum to afford the crude product. The material was purified by semi-preparative HPLC to afford trans ISA$_{TX}$247 (40 mg, 56%) as a white solid: $^1$H NMR (300 MHz, CDCl$_3$) δ 7.95 (d, J=10.2 Hz, 1H), 7.60 (d, J=6.2 Hz, 1H), 7.49 (d, J=8.4 Hz, 1H), 7.16 (d, J=7.9 Hz, 1H), 6.30 (dt, J=17.0, 10.3 Hz, 1H), 5.99 (dd, J=15.4, 10.3 Hz, 1H), 5.73-5.53 (m, 2H), 5.50 (d, J=5.7 Hz, 1H), 5.33 (dd, J=11.6, 3.9 Hz, 1H), 5.16-4.92 (m, 5H), 4.82 (t, J=7.3 Hz, 1H), 4.77 (d, J=13.3 Hz, 1H), 4.65 (t, J=8.7 Hz, 1H), 4.53 (t, J=7.2 Hz, 1H), 3.52 (s, 3H), 3.40 (s, 3H), 3.23 (s, 3H), 3.11 (s, 3H), 3.10 (s, 3H), 2.70 (s, 3H), 2.69 (s, 3H), 2.52-1.98 (m, 8H), 1.82-0.65 (m, 63H); ESI MS m/z 1215 [C$_{63}$H$_{111}$N$_{11}$O$_{12}$+H]$^+$; HPLC 90.6% (AUC), t$_R$=25.14 min.

Example 5

Preparation of the Acetate of trans ISA$_{TX}$247-d$_1$

To a suspension of bis(cyclopentadienyl)zirconiumchloride deuteride (410 mg, 1.60 mmol) in methylene chloride (3 mL) was added propargyltrimethylsilane (0.25 mL, 1.7 mmol), and the mixture was then stirred at room temperature for 10 min. To this solution was sequentially added a solution of acetyl cyclosporin aldehyde from Example 2 (200 mg, 0.160 mmol) in methylene chloride (1 mL) and then silver perchlorate (7 mg, 0.03 mmol). The resulting mixture was stirred at room temperature for 12 h, and then poured into a saturated solution of sodium bicarbonate (10 mL). The organic layer was separated and the aqueous layer was extracted with methylene chloride (3×20 mL). The combined organics were dried over anhydrous sodium sulfate and concentrated under vacuum to afford the crude product. The material was purified by semi-preparative HPLC to afford the acetate of trans ISA$_{TX}$247-d$_1$ (50 mg, 25%) as a colorless oil: $^1$H NMR (300 MHz, CDCl$_3$) δ 8.53 (d, J=9.6 Hz, 1H), 8.04 (d, J=6.9 Hz, 1H), 7.62 (d, J=9.0 Hz, 1H), 7.48 (d, J=7.5 Hz, 1H), 5.90 (d, J=15.2 Hz, 1H), 5.69 (d, J=6.8 Hz, 1H), 5.53 (s, 2H), 5.40-4.72 (m, 7H), 4.64 (d, J=13.3 Hz, 1H), 4.43 (t, J=6.6 Hz, 1H), 3.45 (s, 3H), 3.26 (s, 3H), 3.21 (s, 3H), 3.20 (s, 3H), 3.10 (s, 3H), 2.68 (s, 3H), 2.66 (s, 3H), 2.48-2.33 (m, 1H), 2.22-2.09 (m, 5H), 2.02 (s, 3H), 1.92-0.70 (m, 65H); ESI MS m/z 1258 [C$_{65}$H$_{112}$DN$_{11}$O$_{13}$+H]$^+$.

Example 6

Preparation of traits ISA$_{TX}$247-d$_1$

To a stirred solution of the acetate of trans ISA$_{TX}$247-d$_1$ (43 mg, 0.030 mmol) in methanol (4 mL) was added potassium carbonate (104 mg, 0.750 mmol) at room temperature. After 12 h at room temperature, methanol was evaporated. The crude product was diluted in water (20 mL) and extracted with ethyl acetate (3×50 mL). The combined organics were dried over anhydrous sodium sulfate and concentrated under vacuum to afford the crude product. The material was purified by semi-preparative HPLC to afford trans ISA$_{TX}$247-d$_1$ (17 mg, 47%) as a white solid: $^1$H NMR (300 MHz, CDCl$_3$) δ 7.95 (d, J=9.0 Hz, 1H), 7.62 (d, J=6.8 Hz, 1H), 7.52 (d, J=8.6 Hz, 1H), 7.17 (d, J=7.7 Hz, 1H), 5.98 (d, J=14.8 Hz, 1H), 5.74-5.54 (m, 2H), 5.50 (d, J=5.1 Hz, 1H), 5.33 (d, J=7.9 Hz, 1H), 5.17-4.88 (m, 5H), 4.82 (t, J=6.6 Hz, 1H), 4.74 (d, J=14.1 Hz, 1H), 4.65 (t, J=8.7 Hz, 1H), 4.53 (t, J=7.2 Hz, 1H), 3.52 (s, 3H), 3.40 (s, 3H), 3.24 (s, 3H), 3.11 (s, 3H), 3.10 (s, 3H), 2.71 (s, 3H), 2.69 (s, 3H), 2.55-1.95 (m, 8H), 1.80-0.65 (m, 6311); ESI MS m/z 1216 [C$_{63}$H$_{110}$DN$_{11}$O$_{12}$+H]$^+$; HPLC 95.2% (AUC), t$_R$=24.55 min.

Example 7

Preparation of 1,3-bis(trimethylsilyl)propyne-3,3-d$_2$

To a solution of trimethylsilylacetylene (4.9 mL, 35 mmol) in THF (20 mL) at −78° C. was added dropwise n-butyllithium (24 mL, 1.6 M in hexane, 38 mmol). After 0.5 h at −78° C., iodomethane-d$_3$ (5.0 g, 35 mmol) was added and then the reaction was allowed to warm to room temperature over 1 h. t-Butyllithium (22.4 mL, 1.7 M in pentane, 38 mmol) was added into a −78° C. solution of tetramethylethylenediamine (5.2 mL, 35 mmol) in THF (10 mL) dropwise, and then the resulting solution was added to the reaction mixture via a syringe. After 15 min at −78° C., the reaction was allowed to warm to 0° C. After 1 h at 0° C., the reaction was cooled to −78° C., and then chlorotrimethylsilane (4.4 mL, 35 mmol) was added dropwise. The resulting reaction mixture was stirred at −78° C. for 15 min and allowed to warm to room temperature over 1 h. The reaction was quenched with water (30 mL) and extracted with ether (2×50 mL). The combined organics were washed with water (50 mL) and brine (50 mL), dried over anhydrous sodium sulfate, and concentrated under reduced pressure. The crude product was fractionally distilled to afford 1,3-bis(trimethylsilyl)propyne-3,3-d$_2$ (2.3 g, 52%) as a colorless oil: $^1$H NMR (300 MHz, CDCl$_3$) δ 0.13 (s, 9H), 0.11 (s, 9H).

Example 8

Preparation of 3-(trimethylsilyl)-1-propyne-3,3-d$_2$

To an ice-cooled solution of 1,3-bis(trimethylsilyl)propyne-3,3-d$_2$ from Example 7 (3.6 g, 19 mmol) in ethanol (35 mL) was added a solution of silver nitrate (4.59 g, 27.0 mmol) in water (10 mL) and ethanol (30 mL) in four equal portions 15 min apart, then the mixture was stirred for 15 min at 0° C. A solution of potassium cyanide (8.55 g, 131 mmol) in water (15 mL) was added, and then the mixture was allowed to warm to room temperature. After 2 h at room temperature, water (50 mL) was added and the mixture was extracted with pentane (2×100 mL). The combined organics were washed with water (3×50 mL) and brine (50 mL), dried over anhydrous magnesium sulfate, and filtered. The solvent was distilled through a 8" Vigreux column and the residue was fractionally distilled to afford 3-(trimethylsilyl)-1-propyne-3,3-$d_2$ (1.0 g, 45%) as a colorless oil: $^1$H NMR (300 MHz, CDCl$_3$) δ 1.82 (s, 1H), 0.12 (s, 9H).

Example 9

Preparation of the Acetate of trans ISA$_{TX}$247-$d_2$

To a suspension of bis(cyclopentadienyl)zirconiumchloride hydride (410 mg, 1.60 mmol) in methylene chloride (3 mL) was added 3-(trimethylsilyl)-1-propyne-3,3-$d_2$ from Example 8 (190 mg, 1.70 mmol), and then the mixture was stirred at room temperature for 10 min. To this solution was sequentially added a solution of acetyl cyclosporin aldehyde from Example 2 (200 mg, 0.160 mmol) in methylene chloride (1 mL) and then silver perchlorate (7 mg, 0.03 mmol). The resulting mixture was stirred at room temperature for 12 h, and then poured into a saturated solution of sodium bicarbonate (10 mL). The organic layer was separated and the aqueous layer was extracted with methylene chloride (3×20 mL). The combined organics were dried over anhydrous sodium sulfate and concentrated under vacuum to afford the crude product. The material was purified by semi-preparative HPLC to afford the acetate of trans $ISA_{TX}247$-$d_2$ (75 mg, 37%) as a colorless oil: $^1$H NMR (300 MHz, $CDCl_3$) δ 8.46 (d, J=9.2 Hz, 1H), 8.06 (d, J=6.5 Hz, 1H), 7.83 (d, J=8.4 Hz, 1H), 7.59 (d, J=7.1 Hz, 1H), 6.20 (d, J=10.4 Hz, 1H), 5.90 (dd, J=14.3, 10.4 Hz, 1H), 5.69 (d, J=7.3 Hz, 1H), 5.54 (s, 2H), 5.40-4.75 (m, 5H), 4.65 (d, J=13.6 Hz, 1H), 4.46 (t, J=7.1 Hz, 1H), 3.43 (s, 3H), 3.25 (s, 3H), 3.19 (s, 6H), 3.12 (s, 3H), 2.70 (s, 3H), 2.68 (s, 3H), 2.45-2.28 (m, 1H), 2.22-2.05 (m, 5H), 2.03 (s, 3H), 1.75-0.70 (m, 65H); ESI MS m/z 1259 $[C_{65}H_{111}D_2N_{11}O_{13}+H]^+$.

Example 10

Preparation of trans $ISA_{TX}247$-$d_2$

To a stirred solution of the acetate of trans $ISA_{TX}247$-$d_2$ from Example 9 (70 mg, 0.060 mmol) in methanol (8 mL) was added potassium carbonate (190 mg, 1.40 mmol) at room temperature. After 12 h at room temperature, methanol was evaporated. The crude product was diluted in water (30 mL) and extracted with ethyl acetate (3×100 mL). The combined organics were dried over anhydrous sodium sulfate, and concentrated under vacuum to afford the crude product. The material was purified by semi-preparative HPLC to afford trans $ISA_{TX}247$-$d_2$ (40 mg, 59%) as a white solid: $^1$H NMR (300 MHz, $CDCl_3$) δ 7.98 (d, J=9.2 Hz, 1H), 7.61 (d, J=6.7 Hz, 1H), 7.49 (d, J=7.9 Hz, 1H), 7.17 (d, J=7.7 Hz, 1H), 6.29 (d, J=10.5 Hz, 1H), 5.99 (dd, J=15.2, 10.5 Hz, 1H), 5.73-5.53 (m, 2H), 5.50 (d, J=5.2 Hz, 1H), 5.32 (d, J=8.9 Hz, 1H), 5.16-4.90 (m, 3H), 4.82 (t, J=6.8 Hz, 1H), 4.74 (d, J=14.2 Hz, 1H), 4.64 (t, J=8.6 Hz, 1H), 4.53 (t, J=7.0 Hz, 1H), 3.52 (s, 3H), 3.40 (s, 3H), 3.25 (s, 3H), 3.12 (s, 3H), 3.10 (s, 3H), 2.70 (s, 3H), 2.69 (s, 3H), 2.59-2.35 (m, 2H), 2.20-1.92 (m, 6H), 1.82-0.65 (m, 63H); ESI MS m/z 1217 $[C_{63}H_{109}D_2N_{11}O_{12}+H]^+$; HPLC 93.4% (AUC), $t_R$=25.18 min.

Example 11

Preparation of the Acetate of trans $ISA_{TX}247$-$d_3$

To a suspension of bis(cyclopentadienyl)zirconiumchloride deuteride (410 mg, 1.60 mmol) in methylene chloride (3 mL) was added 3-(trimethylsilyl)-1-propyne-3,3-$d_2$ from Example 8 (190 mg, 1.70 mmol), and then the mixture was stirred at room temperature for 10 min. To this solution was sequentially added a solution of acetyl cyclosporin aldehyde from Example 2 (200 mg, 0.160 mmol) in methylene chloride (1 mL) and then silver perchlorate (7 mg, 0.03 mmol). The resulting mixture was stirred at room temperature for 12 h, and then poured into a saturated solution of sodium bicarbonate (10 mL). The organic layer was separated and the aqueous layer was extracted with methylene chloride (3×20 mL). The combined organics were dried over anhydrous sodium sulfate and concentrated under vacuum to afford the crude product. The material was purified by semi-preparative HPLC to afford the acetate of trans $ISA_{TX}247$-$d_3$ (51 mg, 25%) as a colorless oil: $^1$H NMR (300 MHz, $CDCl_3$) δ 8.53 (d, J=9.2 Hz, 1H), 8.06 (d, J=6.8 Hz, 1H), 7.68 (d, J=9.0 Hz, 1H), 7.52 (d, J=7.6 Hz, 1H), 5.90 (d, J=15.2 Hz, 1H), 5.69 (dd, J=11.2, 3.7 Hz, 1H), 5.54 (s, 2H), 5.42-4.75 (m, 5H), 4.66 (d, J=13.9 Hz, 1H), 4.44 (t, J=7.1 Hz, 1H), 3.45 (s, 3H), 3.26 (s, 3H), 3.24 (s, 6H), 3.11 (s, 3H), 2.68 (s, 3H), 2.67 (s, 3H), 2.45-2.35 (m, 1H), 2.28-2.05 (m, 5H), 2.02 (s, 3H), 1.95-0.65 (m, 65H); ESI MS m/z 1260 $[C_{65}H_{110}D_3N_{11}O_{13}+H]^+$.

Example 12

Preparation of trans $ISA_{TX}247$-$d_3$

To a stirred solution of acetate of trans $ISA_{TX}247$-$d_3$ from Example 11 (45 mg, 0.040 mmol) in methanol (5 mL) was added potassium carbonate (120 mg, 0.900 mmol) at room temperature. After 12 h at room temperature, methanol was evaporated. The crude product was diluted in water (30 mL) and extracted with ethyl acetate (3×100 mL). The combined organics were dried over anhydrous sodium sulfate, and concentrated under vacuum to afford the crude product. The material was purified by semi-preparative HPLC to afford trans $ISA_{TX}247$-$d_3$ (19 mg, 43%) as a white solid: $^1$H NMR (300 MHz, $CDCl_3$) δ 7.98 (d, J=9.6 Hz, 1H), 7.61 (d, J=7.2 Hz, 1H), 7.49 (d, J=7.9 Hz, 1H), 7.15 (d, J=8.1 Hz, 1H), 5.99 (d, J=15.0 Hz, 1H), 5.74-5.55 (m, 2H), 5.50 (d, J=5.9 Hz, 1H), 5.30 (dd, J=10.9, 3.2 Hz, 1H), 5.16-4.90 (m, 3H), 4.82 (t, J=7.2 Hz, 1H), 4.73 (d, J=13.9 Hz, 1H), 4.65 (t, J=9.3 Hz, 1H), 4.53 (t, J=7.3 Hz, 1H), 3.52 (s, 3H), 3.40 (s, 3H), 3.25 (s, 3H), 3.11 (s, 3H), 3.10 (s, 3H), 2.70 (s, 3H), 2.69 (s, 3H), 2.57-2.40 (m, 2H), 2.20-1.94 (m, 6H), 1.82-0.65 (m, 63H); ESI MS m/z 1218 $[C_{63}H_{108}D_3N_{11}O_{12}+H]^+$; HPLC>99% (AUC), $t_R$=24.58 min.

Example 13

Preparation of Acetyl Cyclosporin α,β-Unsaturated Aldehyde

A mixture of acetyl cyclosporin A from Example 1 (100 mg, 0.08 mmol), 2-vinyl-1,3-dioxolane (0.04 mL, 0.4 mmol), Hoveyda-Grubbs' $2^{nd}$ generation catalyst (5 mg, 0.008 mmol), and toluene (1 mL) was heated at 60° C. under nitrogen for 12 h. The catalyst (5 mg) was refilled, and the mixture was stirred for an additional 12 h, cooled to room temperature, and concentrated in vacuo. The residue was purified by semi-preparative HPLC to afford acetyl cyclosporin α,β-unsaturated aldehyde (89 mg, 88%) as an off-white solid: $^1$H NMR (300 MHz, CDCl$_3$) δ 9.42 (d, J=7.9 Hz, 1H), 8.55 (d, J=9.6 Hz, 1H), 8.02 (d, J=6.8 Hz, 1H), 7.71 (d, J=8.8 Hz, 1H), 7.53 (d, J=7.5 Hz, 1H), 6.73 (ddd, J=15.5, 10.0, 4.5 Hz, 1H), 5.60 (dd, J=15.5, 7.9 Hz, 1H), 5.70-4.40 (m, 12H), 3.46 (s, 3H), 3.27 (s, 3H), 3.22 (s, 3H), 3.21 (s, 3H), 3.13 (s, 3H), 2.68 (s, 3H), 2.66 (s, 3H), 2.50-1.50 (m, 10H), 2.04 (s, 3H), 1.40-0.75 (m, 58H); ESI MS m/z 1259 [C$_{64}$H$_{111}$N$_{11}$O$_{14}$+H]$^+$.

Example 14

Preparation of Acetyl Cyclosporin α,β-Unsaturated Aldehyde

A mixture of acetyl cyclosporin A from Example 1 (100 mg, 0.08 mmol), acrolein dimethyl acetal (0.018 mL, 0.16 mmol), Grubbs' catalyst 2$^{nd}$ generation (25 mg, 0.029 mmol), and methylene chloride (1 mL) was heated at 60° C. in a sealed tube for 12 h. The catalyst (25 mg) and acrolein dimethyl acetal (0.018 mL) were refilled, and the mixture was stirred at the same temperature for an additional 12 h, cooled to room temperature, and concentrated in vacuo. The residue was purified by semi-preparative HPLC to afford acetyl cyclosporin α,β-unsaturated aldehyde (65 mg, 64%) as an off-white solid.

Example 15

Preparation of the Acetate of trans ISA$_{TX}$247

Sodium bis(trimethylsilyl)amide (1.0 M in THF, 0.32 mL, 0.32 mmol) was added to a suspension of methyltriphenylphosphonium bromide in THF (1 mL) at room temperature. The mixture was stirred under nitrogen for 2 h and then cooled to 0° C. Acetyl cyclosporin α,β-unsaturated aldehyde from Example 13 (80 mg, 0.064 mmol) in THF (1 mL) was added, and the mixture was stirred at 0° C. for 15 min. The reaction was quenched with a saturated solution of ammonium chloride and extracted with ethyl acetate. The combined organic layers were washed with brine, dried over anhydrous sodium sulfate, and concentrated in vacuo. The residue was purified by semi-preparative HPLC to afford the acetate of trans ISA$_{TX}$247 (25 mg, 31%) as a white solid.

Example 16

Preparation of Acetyl Cyclosporin α,β-Unsaturated Aldehyde

To an ice-cooled suspension of bis(cyclopentadienyl)zirconiumchloride hydride (413 mg, 1.60 mmol) in methylene chloride (4 mL) was added ethyl ethynyl ether (50% in hexanes, 0.33 mL, 1.68 mmol), and then the mixture was allowed to warm to room temperature over 10 min. To this solution was sequentially added a solution of cyclosporin aldehyde from Example 2 (200 mg, 0.16 mmol) in methylene chloride (2 mL) and then silver perchlorate (7 mg, 0.03 mmol). The resulting mixture was stirred at room temperature for 12 h. The reaction mixture was diluted with ethyl ether (30 mL), and then washed with a saturated solution of sodium bicarbonate (20 mL). The organic layer was filtered through diatomaceous earth, and then mixed with 3 N HCl solution (30 mL). The two-phase mixture was stirred under nitrogen for 4 h. The organic layer was separated and washed with a saturated solution of sodium bicarbonate and brine, then dried over anhydrous sodium sulfate and concentrated. The crude product was purified by semi-preparative HPLC to afford the acetyl cyclosporin α,β-unsaturated aldehyde, which is the same as the product of Example 13.

Example 17

Preparation of Acetyl Cyclosporin Triene

To a suspension of bis(cyclopentadienyl)zirconiumchloride hydride (206 mg, 0.80 mmol) in methylene chloride (2 mL) was added propargyl trimethylsilane (0.13 mL, 0.84 mmol), and then the mixture was stirred at room temperature for 10 min. To this solution was sequentially added a solution of acetyl cyclosporin α,β-unsaturated aldehyde from Example 13 (100 mg, 0.08 mmol) in methylene chloride (1 mL) and then silver perchlorate (3 mg, 0.016 mmol). The resulting mixture was stirred at room temperature for 12 h, and then poured into a saturated solution of sodium bicarbonate (10 mL). The organic layer was separated and the aqueous layer was extracted with methylene chloride (2×20 mL). The combined organics were dried over anhydrous sodium sulfate and concentrated under vacuum to afford the crude product. The material was purified by semi-preparative HPLC to afford acetyl cyclosporin triene (30 mg, 29%) as a white solid: $^1$H NMR (300 MHz, CDCl$_3$) δ 8.53 (d, J=9.6 Hz, 1H), 8.05 (d, J=6.7 Hz, 1H), 7.70 (d, J=9.1 Hz, 1H), 7.52 (d, J=7.5 Hz, 1H), 6.36 (dt, J=16.8, 9.8 Hz, 1H), 6.17 (dd, J=14.8, 9.9 Hz, 1H), 6.08 (dd, J=14.7, 9.7 Hz, 1H), 5.92 (dd, J=14.6, 9.7 Hz, 1H), 5.69 (dd, J=10.7, 3.6 Hz, 1H), 5.53 (s, 2H), 5.40-4.75 (m, 7H), 4.65 (d, J=14.2 Hz, 1H), 4.44 (t, J=7.3 Hz, 1H), 3.45 (s, 3H), 3.25 (s, 3H), 3.21 (s, 3H), 3.20 (s, 3H), 3.11 (s, 3H), 2.68 (s, 3H), 2.67 (s, 3H), 2.48-2.33 (m, 1H), 2.25-2.10 (m, 4H), 2.03 (s, 3H), 1.75-0.70 (m, 66H); ESI MS m/z 1283 [C$_{67}$H$_{115}$N$_{11}$O$_{13}$+H]$^+$.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A process for preparation of a trans ISA$_{TX}$247 compound of the formula:

Formula Ib

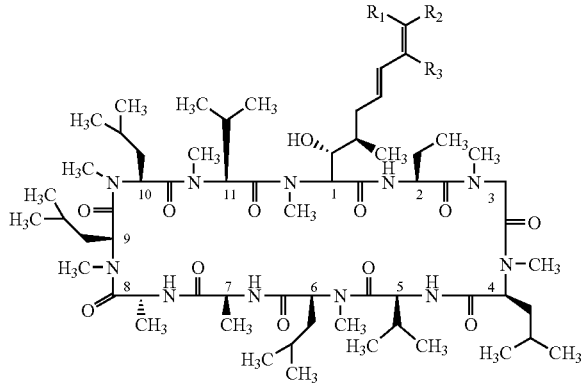

wherein:
R$_1$=H or D;
R$_2$=H or D; and
R$_3$=H or D, said process comprising:

reacting a first intermediate compound of the formula:

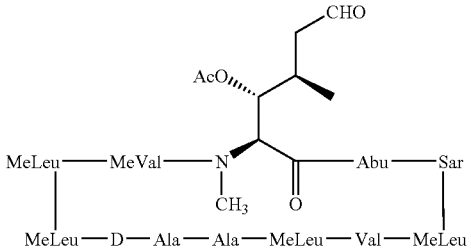

with an organozirconium reagent, under conditions effective to produce a second intermediate compound of the formula:

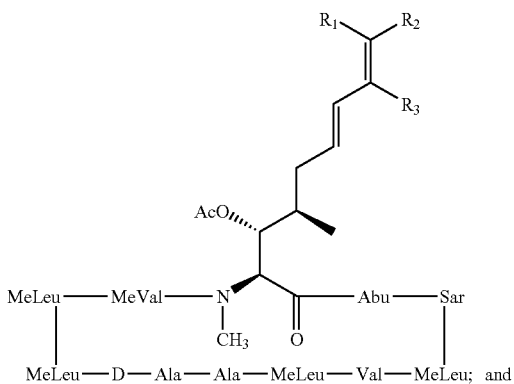

deacetylating the second intermediate compound, under conditions effective to produce the trans $ISA_{TX}247$ compound.

2. The process according to claim 1 further comprising:

carrying out oxidation on a third intermediate compound of the formula:

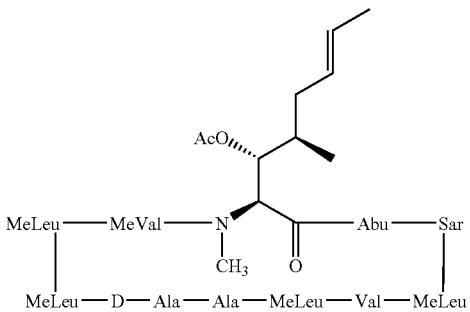

under conditions effective to produce the first intermediate compound.

3. The process according to claim 2 further comprising:

acetylating a fourth intermediate compound of the formula:

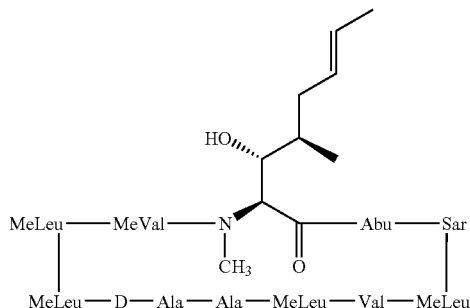

under conditions effective to produce the third intermediate compound.

4. The process according to claim 1, wherein the organozirconium reagent comprises a zirconium reagent and an alkyne reagent.

5. The process according to claim 4, wherein the zirconium reagent is $Cp_2Zr(H)Cl$ or $Cp_2Zr(D)Cl$.

6. The process according to claim 4, wherein the alkyne reagent is propargyl trimethylsilane or propargyl trimethylsilane-$d_2$.

7. The process according to claim 1, wherein said reacting is carried out with $Cp_2Zr(H)Cl$ and propargyl trimethylsilane, under conditions effective to produce the trans $ISA_{TX}247$ compound, wherein $R_1=R_2=R_3=H$.

8. The process according to claim 1, wherein said reacting is carried out with $Cp_2Zr(D)Cl$ and propargyl trimethylsilane, under conditions effective to produce the trans $ISA_{TX}247$ compound, wherein $R_1=R_2=H$ and $R_3=D$.

9. The process according to claim 1, wherein said reacting is carried out with $Cp_2Zr(H)Cl$ and propargyl trimethylsilane-$d_2$, under conditions effective to produce the trans $ISA_{TX}247$ compound, wherein $R_1=R_2=D$ and $R_3=H$.

10. The process according to claim 1, wherein said reacting is carried out with $Cp_2Zr(D)Cl$ and propargyl trimethylsilane-$d_2$, under conditions effective to produce the trans $ISA_{TX}247$ compound, wherein $R_1=R_2=R_3=D$.

11. The process according to claim 1, wherein said reacting is carried out in the presence of a silver salt catalyst.

12. The process according to claim 11, wherein the silver salt catalyst is selected from the group consisting of $AgClO_4$, AgOTf, $AgBF_4$, $AgPF_6$, $AgAsF_6$, and $AgSbF_6$.

13. A process for preparation of an acetyl cyclosporin α,β-unsaturated aldehyde compound of the formula:

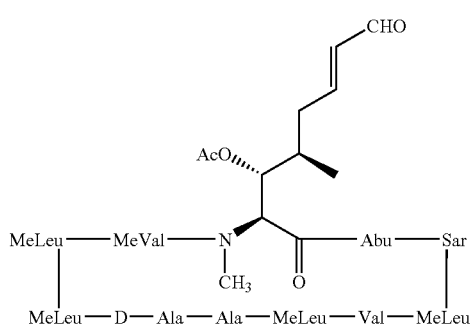

said process comprising:
reacting a first intermediate compound of the formula:

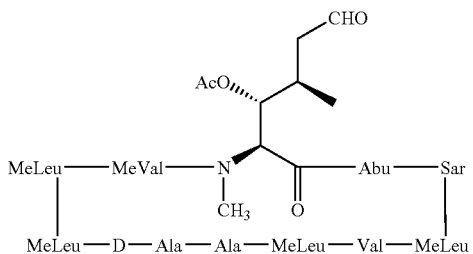

with an organozirconium reagent, under conditions effective to produce the acetyl cyclosporin α,β-unsaturated aldehyde compound.

14. The process according to claim 13, wherein the organozirconium reagent comprises a zirconium reagent and an alkyne reagent.

15. The process according to claim 14, wherein the zirconium reagent is $Cp_2Zr(H)Cl$.

16. The process according to claim 14, wherein the alkyne reagent is methoxyethyne or ethoxyethyne.

17. The process according to claim 13, wherein said reacting is carried out in the presence of a silver salt catalyst.

18. The process according to claim 17, wherein the silver salt catalyst is selected from the group consisting of $AgClO_4$, $AgOTf$, $AgBF_4$, $AgPF_6$, $AgAsF_6$, and $AgSbF_6$.

19. A process for preparing a cyclosporin triene analogue compound of the formula:

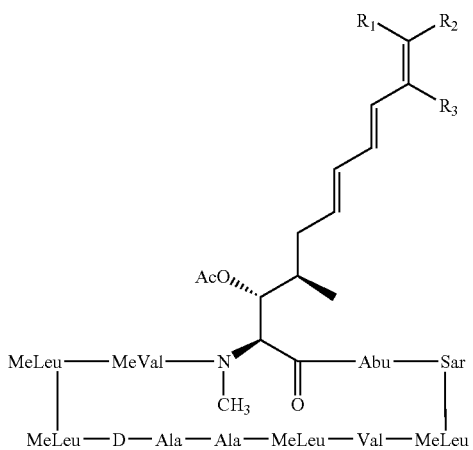

wherein:
$R_1$=H or D;
$R_2$=H or D; and
$R_3$=H or D,
said process comprising:
reacting a first intermediate compound of the formula:

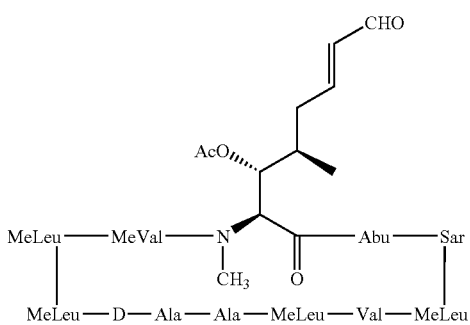

with an organozirconium reagent, under conditions effective to produce the cyclosporin triene analogue compound.

20. The process according to claim 19, wherein the organozirconium reagent comprises a zirconium reagent and an alkyne reagent.

21. The process according to claim 20, wherein the zirconium reagent is $Cp_2Zr(H)Cl$ or $Cp_2Zr(D)Cl$.

22. The process according to claim 20, wherein the alkyne reagent is propargyl trimethylsilane or propargyl trimethylsilane-$d_2$.

23. The process according to claim 19, wherein said reacting is carried out in the presence of a silver salt catalyst.

24. The process according to claim 23, wherein the silver salt catalyst is selected from the group consisting of $AgClO_4$, $AgOTf$, $AgBF_4$, $AgPF_6$, $AgAsF_6$, and $AgSbF_6$.

* * * * *